(12) United States Patent
Kim et al.

(10) Patent No.: US 11,230,740 B2
(45) Date of Patent: Jan. 25, 2022

(54) APOPTOSIS REGULATORY GENE DETECTED IN IRRADIATED-THYMIC LYMPHOMA CELL AND METHOD FOR DETECTING SAME

(71) Applicant: KOREA HYDRO & NUCLEAR POWER CO., LTD., Gyeongsangbuk-do (KR)

(72) Inventors: Hee Sun Kim, Gyeonggi-do (KR); Hoon Choi, Seoul (KR); Kwang Hee Yang, Seoul (KR); Yun-Mi Baek, Seoul (KR); Dong-Kwon Keum, Daejeon (KR); Hee Youn Shim, Seoul (KR); Byulnim Hwang, Seoul (KR)

(73) Assignee: KOREA HYDRO & NUCLEAR POWER CO., LTD., Gyeongsangbuk-Do (KR)

( * ) Notice: Subject to any disclaimer, the term of this patent is extended or adjusted under 35 U.S.C. 154(b) by 342 days.

(21) Appl. No.: 16/312,126

(22) PCT Filed: Sep. 8, 2016

(86) PCT No.: PCT/KR2016/010072
§ 371 (c)(1),
(2) Date: Dec. 20, 2018

(87) PCT Pub. No.: WO2018/004062
PCT Pub. Date: Jan. 4, 2018

(65) Prior Publication Data
US 2019/0233901 A1  Aug. 1, 2019

(30) Foreign Application Priority Data
Jun. 29, 2016 (KR) .................. 10-2016-0081973

(51) Int. Cl.
*C12Q 1/68* (2018.01)
*C12Q 1/6886* (2018.01)
*G01N 33/574* (2006.01)

(52) U.S. Cl.
CPC ..... *C12Q 1/6886* (2013.01); *G01N 33/57407* (2013.01); *C12Q 2600/142* (2013.01); *C12Q 2600/148* (2013.01); *C12Q 2600/158* (2013.01)

(58) Field of Classification Search
None
See application file for complete search history.

(56) References Cited

U.S. PATENT DOCUMENTS

| 6,994,957 | B2 | 2/2006 | Korneluk et al. |
| 9,314,489 | B2 | 4/2016 | Kelly et al. |
| 2016/0120949 | A1 | 5/2016 | Basile |

FOREIGN PATENT DOCUMENTS

| JP | 2012-165666 A1 | 9/2012 |
| KR | 1020110126328 A | 11/2011 |
| KR | 1020120085004 A | 7/2012 |
| KR | 1020130019518 A | 2/2013 |
| KR | 1020130086688 A | 8/2013 |

OTHER PUBLICATIONS

GenBank NM_007546. Feb. 26, 2014. Mus musculus BCL-2 interacting killer (Bik), mRNA. three pages. (Year: 2014).*
Bom et al. Korean J Nucl. Med 2000, p. 144-153. (Year: 2000).*
Revision History for GenBank record NM_007546.2. Obtained from https://www.ncbi.nlm.nih.gov/nuccore/NM_007546.2?report= girevhist on Feb. 22, 2021. 2 pages. (Year: 2021).*
Bong et al. (Journal of Radiation Protection, vol. 37 No. 2 Jun. 2012, pp. 56-62) (Year: 2012).*
Chinnadurai et al. (NIH Public Access Author Manuscript. Author Manuscript. Oncogene. Author manuscript; available in PMC Aug. 26, 2010. pp. 1-16) (Year: 2010).*
Lee et al. (Biochemical Pharmacology 75(2008) 2020-2033 (Year: 2008).*
Shin, S. et al., Differential Expression of Immune-Associated Cancer Regulatory Genes in Low-Versus High-Dose-Rate Irradiated AKR/J Mice, Genomics, 2011, pp. 358-363.
Bom, H. et al., Relationship Between Radiation Induced Activation of DNA Repair Genes and Radiation Induced Apoptosis in Human Cell Line A431, Korean J. Nucl. Med., 2000, pp. 144-153.
Sakai, K. et al., Enhancement of Bio-Protective Functions by Low Dose/Dose-Rate Radiation, Dose-Response, 2006, pp. 327-332.
Sakai, K. et al., Suppression of Carcinogenic Processes in Mice by Chronic Low Dose Rate Gamma-Irradiation, Int. J. Low Radiation, 2003, pp. 142-146, vol. 1, No. 1.
Scott, B.R., Low-Dose Radiation Stimulated Natural Chemical And Biological Protection Against Lung Cancer, Dose-Response, 2008, pp. 299-318.
Le, X. Chris et al., Inducible Repair of Thymine Glycol Detected by an Ultrasensitive Assay for DNA Damage, Science Mag, May 15, 1998, pp. 1066-1069, vol. 280.

(Continued)

*Primary Examiner* — Juliet C Switzer
(74) *Attorney, Agent, or Firm* — Standley Law Group LLP

(57) ABSTRACT

An apoptosis regulatory gene is detected in an irradiated-thymic lymphoma cell by a method for detecting such an apoptosis regulatory gene in a low-dose-rate and low-level-irradiated thymic lymphoma cell of a mouse. This has an effect of revealing the function of an apoptosis regulatory gene by means of irradiation and providing a gene profile, by detecting an apoptosis regulatory gene detected in an irradiated-thymic lymphoma cell. The detected apoptosis regulatory gene is used to construct a gene profile that can assess the dose-response relationship of industrial and healthcare workers living in a low level-radiation environment. The detected apoptosis regulatory gene can be used as an index for evaluating the extent of cancer progression and the degree of treatment in patients with thymic lymphoma. The method for detecting such an apoptosis regulatory gene is used to prepare a composition for diagnosing thymic lymphoma and a diagnostic kit.

3 Claims, 6 Drawing Sheets
Specification includes a Sequence Listing.

(56) References Cited

OTHER PUBLICATIONS

Nogami, M. et al., Mice Chronically Exposed to Low Dose Ionizing Radiation Possess Splenocytes With Elevated Levels of HSP70 mRNA, HSC70 and HSP72 and With an Increased Capacity to Proliferate, Int. J. Radiat. Biol., 1993, pp. 775-783, vol. 63, No. 6.
Nogami, M. et al., T Cells are the Cellular Target of the Proliferation-Augmenting Effect of Chronic Low-Dose Ionizing Radiation in Mice, Radiation Research, 1994, pp. 47-52, vol. 139.
Labi, V. et al., Loss of the BH3-only protein Bmf impairs B cell homeostasis and accelerates γ Irradiation-Induced Thymic Lymphoma Development, The Journal of Experimental Medicine, Feb. 25, 2008, vol. 205, No. 3.

\* cited by examiner

APOPTOSIS REGULATORY GENE DETECTED IN IRRADIATED-THYMIC LYMPHOMA CELL AND METHOD FOR DETECTING SAME

TECHNICAL FIELD

The present invention relates to an apoptosis regulatory gene detected in irradiated thymic lymphoma cells, and more particularly to a method of detecting an apoptosis regulatory gene in low-dose-rate low-level-irradiated mouse thymic lymphoma cells.

BACKGROUND ART

Generally, high levels of radiation are known to damage DNA and cause cancer. In contrast, low-dose radiation is known to suppress cancer, but the genes involved and the mechanism of cancer suppression are unknown.

Low-dose radiation indicates radiation having low intensity, typically radiation of 100 mSv or less. A large amount of radiation may harm organisms, but low-dose radiation has beneficial effects, such as promoting the physiological activity of organisms to thus prolong the lifespan thereof, or promoting growth or reducing the incidence of tumors. These effects are referred to as radiation hormesis.

Low-dose radiation in the range of milligray (mGy), unlike high-dose radiation, has been reported to increase disease resistance and elicit adaptive protection effects (Sakai K., et al., Dose Response, 2006, 4(4):327-332; Sakai K., et al, Int. J. Low Radiat., 2003, 1(1):142-146; Scott B R., Dose Response, 2008 6(3):299-318), and experimental mice with diabetic genetic factors have been reported to show amelioration in disease after irradiation with a predetermined amount of low-dose radiation (Sakai K., et al., Dose Response, 2006, 4(4):327-332). Furthermore, there have been reports in which radiation of 0.25 Gy or less is effective at preventing DNA damage and restoring damaged DNA (Le X C., et al., Science, 1998, 280(5366):1066-1069), and also in which low-dose radiation is effective at immune enhancement (Nogami M., et al., Int. J. Radiat. Biol., 1993, 63(6): 775-783; Nogami M., et al., Radiat. Res., 1994, 139(1):47-52).1. Low-dose radiation).

DISCLOSURE

Technical Problem

Accordingly, the present invention is intended to provide an apoptosis regulatory gene detected in irradiated thymic lymphoma cells, and more particularly a method of detecting an apoptosis regulatory gene in low-dose-rate low-level-irradiated thymic cancer cells.

In addition, the present invention is intended to provide a composition for the diagnosis of thymic lymphoma, comprising the base sequence of an apoptosis regulatory gene or a base sequence complementary thereto. In addition, the present invention is intended to provide a kit for the diagnosis of thymic lymphoma, comprising the above composition.

Technical Solution

Therefore, the present invention provides a method of detecting an apoptosis regulatory gene in thymic lymphoma cells, comprising applying low-dose-rate low-level radiation to thymic lymphoma cells and detecting an apoptosis regulatory gene having altered gene expression in individual irradiated mouse thymic lymphoma cells.

The thymic lymphoma cells are preferably a mouse (*Mus musculus*) thymic lymphoma EL4 cell line. The low-dose-rate low-level radiation may be applied such that a final cumulative dose is 61.92 mGy at a dose rate of 2.58 mGy/hr, 139.2 mGy at a dose rate of 5.8 mGy/hr, and 557.28 mGy at a dose rate of 23.22 mGy/hr.

The detecting the apoptosis regulatory gene may include performing polymerase chain reaction and Western blotting.

In the detecting the apoptosis regulatory gene, the detected gene preferably includes Bik (Genebank accession No: NM_007546), Bmf (Genebank accession No: NM_138313), Ddit3 (Genebank accession No: NM_007837), Nod1 (Genebank accession No: NM_172729), and Tnfrsf19 (Genebank accession No: NM_013869).

In addition, the present invention provides a composition for the diagnosis of thymic lymphoma, comprising the base sequence of at least one apoptosis regulatory gene selected from the group consisting of apoptosis regulatory genes of thymic lymphoma, including Bik (Genebank accession No: NM_007546), Bmf (Genebank accession No: NM_138313), Ddit3 (Genebank accession No: NM_007837), Nod1 (Genebank accession No: NM_172729) and Tnfrsf19 (Genebank accession No: NM_013869) or the base sequence complementary thereto.

In addition, the present invention provides a diagnostic kit for the diagnosis of thymic lymphoma, comprising the above composition for the diagnosis of thymic lymphoma.

Advantageous Effects

According to the present invention, an apoptosis regulatory gene can be detected in irradiated thymic lymphoma cells, thereby revealing the function of the apoptosis regulatory gene by irradiation and providing a gene profile.

Also, the apoptosis regulatory gene detected in irradiated thymic lymphoma cells can be used to construct a gene profile that enables assessment of a dose-response relationship of industrial and healthcare workers in low-level radiation environments.

The apoptosis regulatory gene detected in irradiated thymic lymphoma cells can be used as a measure of cancer progression and treatment in patients with thymic lymphoma.

The method of detecting the apoptosis regulatory gene in irradiated thymic lymphoma cells can be used to manufacture a composition for the diagnosis of thymic lymphoma and a diagnostic kit.

BEST MODE

Figure 1A:
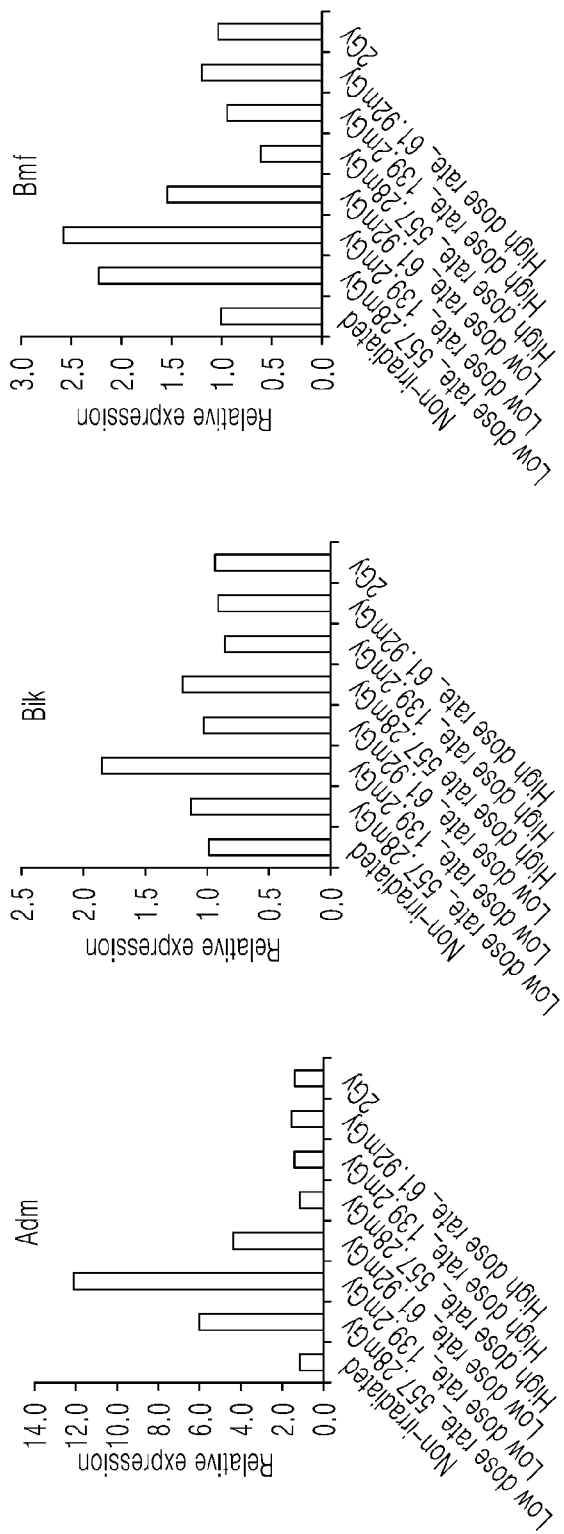
FIGS. 1A to 1D show changes in RNA-level expression of apoptosis regulatory genes depending on the dose rate and the cumulative dose.
Figure 1B:
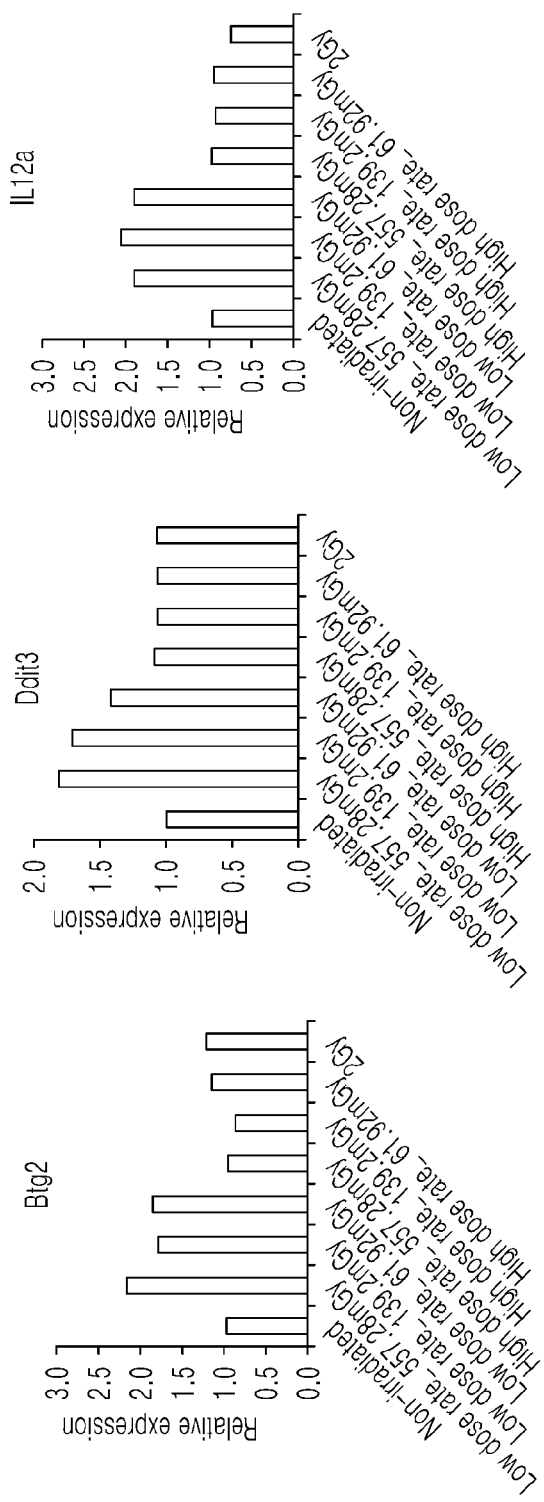
Figure 1C:
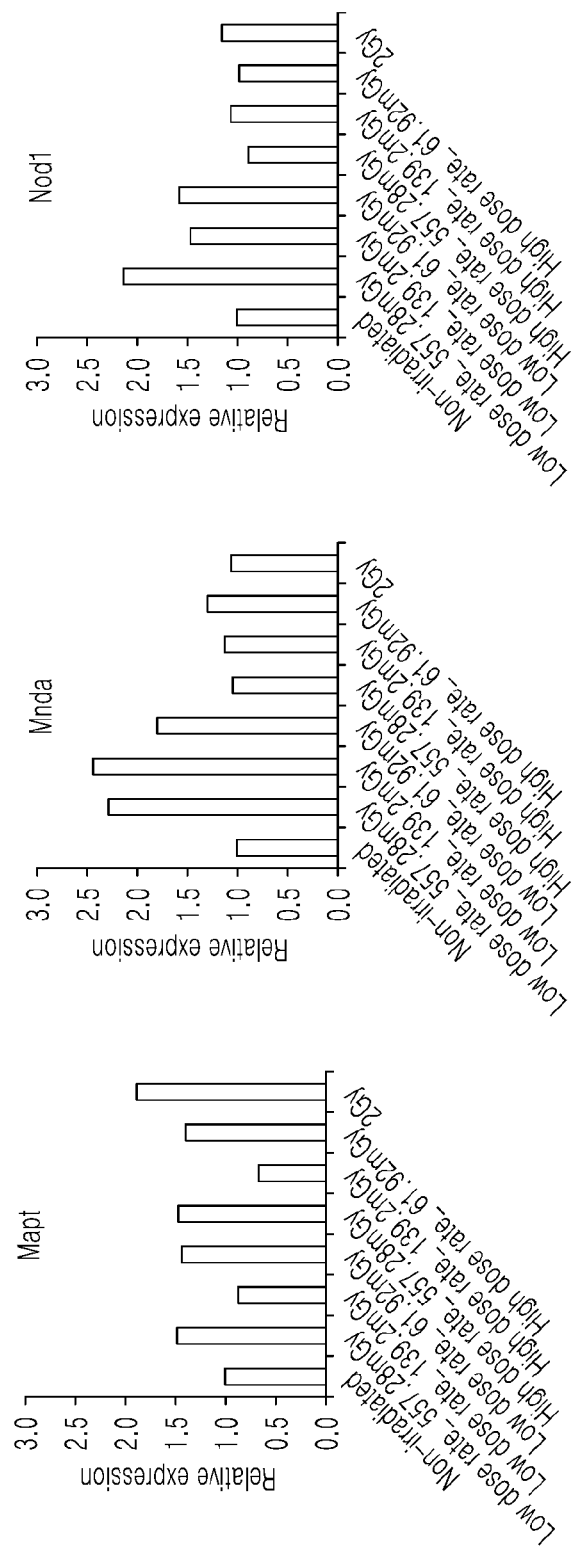
Figure 1D:
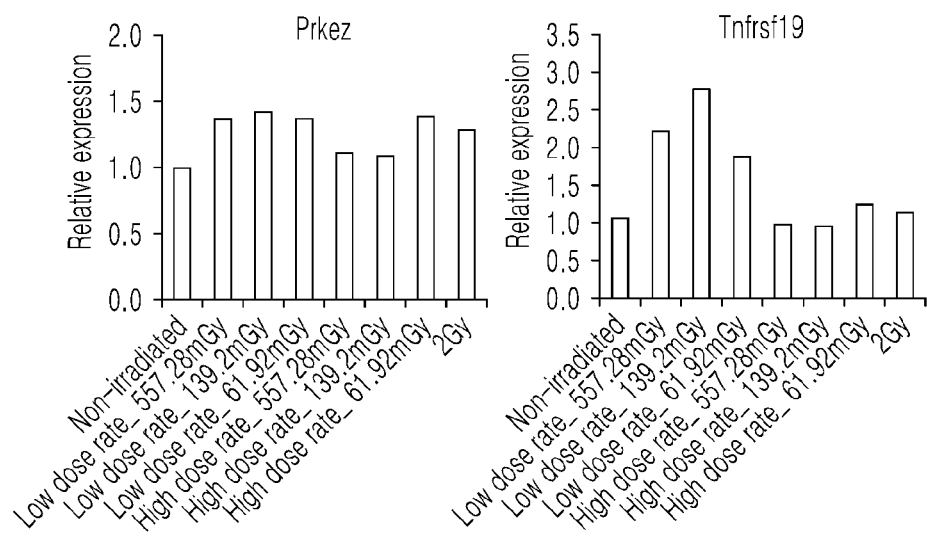

Hereinafter, a detailed description will be given of the present invention.

An embodiment of the present invention pertains to a method of detecting an apoptosis regulatory gene in thymic lymphoma cells, comprising applying low-dose-rate low-level radiation, high-dose-rate low-level radiation and high-dose-rate high-level radiation to thymic lymphoma cells and detecting an apoptosis regulatory gene having altered gene expression in individual irradiated mouse thymic lymphoma cells.

The thymic lymphoma cells are preferably derived from mouse (Mus musculus) thymic lymphoma.

As the mouse thymic lymphoma cells, the EL4 cell line is a T-cell line established in lymphoma of C57BL/6, which is a pure mouse to which a chemical carcinogen is administered, and expresses Thy-1, 2 and H2b on the cell surface, and is reactive to phytohemagglutinin (PHA). This cell line produces interleukin-2 (IL-2) and is used for cell-mediated immunity experiments.

The low-dose-rate low-level radiation is preferably applied such that a final cumulative dose is 61.92 mGy at a dose rate of 2.58 mGy/hr, 139.2 mGy at a dose rate of 5.8 mGy/hr, and 557.28 mGy at a dose rate of 23.22 mGy/hr.

The detecting the apoptosis regulatory gene may be performed through polymerase chain reaction and Western blotting.

In the detecting the apoptosis regulatory gene, the detected gene may include Bik ((Genebank accession No: NM_007546), Bmf (Genebank accession No: NM_138313), Ddit3 (Genebank accession No: NM_007837), Nod1 (Genebank accession No: NM_172729), and Tnfrsf19 (Genebank accession No: NM_013869).

Another embodiment of the present invention pertains to a composition for the diagnosis of thymic lymphoma, comprising the base sequence of at least one apoptosis regulatory gene selected from the group consisting of apoptosis regulatory genes of thymic lymphoma, including Bik ((Genebank accession No: NM_007546), Bmf (Genebank accession No: NM_138313), Ddit3 (Genebank accession No: NM_007837), Nod1 (Genebank accession No: NM_172729) and Tnfrsf19 (Genebank accession No: NM_013869) or the base sequence complementary thereto.

A better understanding of the present invention will be given through the following examples, which are merely set forth to illustrate the present invention but are not to be construed as limiting the scope of the present invention, as will be apparent to those skilled in the art.

Example 1

Mouse Thymic Lymphoma Cell Culture and Irradiation

Mouse thymic lymphoma cells (EL4) (TIB-39, ATCC) were cultured using a cell incubator at 37° C. under 5% $CO_2$ using an RPMI 1640 medium containing 10% fetal bovine serum and 1% penicillin/streptomycin. The cultured cells were prepared at a concentration of $10^5$ cells/ml.

For the low-dose-rate low-level-irradiated cell group, low-dose-rate low-level radiation (2.58 mGy/hr, 5.8 mGy/hr, 23.22 mGy/hr) was applied for 24 hr to the cells prepared as above such that the cumulative dose of the cells was 61.92 mGy, 139.2 mGy and 557.28 mGy.

For the high-dose-rate low-level-irradiated cell group, in comparison with the low-dose-rate low-level-irradiated cell group, high-dose-rate low-level radiation (0.8 Gy/min) was applied to the cells prepared as described above such that the final cumulative dose was 61.92 mGy, 139.2 mGy and 557.28 mGy.

For the high-dose-rate high-level-irradiated cell group, high-dose-rate high-level radiation (0.8 Gy/min) was applied such that the final cumulative dose was 2 Gy.

Example 2

Screening of Apoptosis Regulatory Gene of Irradiated Mouse Thymic Lymphoma Cells and Measurement of RNA-level Expression Thereof 2-1 Screening of Apoptosis Regulatory Gene of Irradiated Mouse Thymic Lymphoma Cells In order to screen the apoptosis regulatory gene of irradiated cells, a microarray was performed.

Total RNA of the low-dose-rate low-level-irradiated cell group of Example 1 was extracted and labeled with Cyanine3. A microarray chip in which all the genes of total DNA were arranged was prepared, and the Cyanine3-labeled total RNA was allowed to react therein. The signal in response to the above reaction was analyzed and the extent of expression of each RNA was verified.

Furthermore, the high-dose-rate low-level-irradiated cell group and the high-dose-rate high-level-irradiated cell group were subjected to microarray in the same manner as above.

Based on the results of microarray, genes, the expression of which was increased two times or more in the low-dose-rate low-level-irradiated cell group compared to the non-irradiated cell group, were selected. The selected genes were Adm, Btg2, II12a, Mapt, Mnda, Bmf, Nod1, Bik, Ddit3, Prkcz, and Tnfrsf19.

2-2 Measurement of RNA-Level Expression of Apoptosis Regulatory Gene of Irradiated Mouse Thymic Lymphoma Cells In order to verify RNA-level expression of 11 genes selected through microarray, polymerase chain reaction (PCR) was performed.

Using a high-capacity cDNA reverse transcription kit (Applied Biosystems, USA), RNA of the apoptosis regulatory gene was subjected to reverse transcription. Then, PCR of RNA subjected to reverse transcription was carried out using primers shown in Table 1 below. The PCR results were normalized using the housekeeping gene GAPDH.

Furthermore, in the high-dose-rate low-level-irradiated cell group and the high-dose-rate high-level-irradiated cell group, the amount of apoptosis regulatory gene expression was measured in the same manner as above.

TABLE 1

Base sequence of primer used in PCR for measurement of expression of apoptosis regulatory gene

| Gene | Gene No. | Forward (5'→3') | Sequence Identifier |
|---|---|---|---|
| Adm | NM_009627 | TCGCTGATGAGACGACAGTT | 1 |
| Bik | NM_007546 | ATGGCCAGAGACGTCATCAA | 3 |
| Bmf | NM_138313 | CTCTCTGCTGACCTGTTTGC | 5 |

TABLE 1-continued

Base sequence of primer used in PCR for measurement of expression of apoptosis regulatory gene

| Gene | | | Sequence Identifier |
|---|---|---|---|
| Btg2 | NM_007570 | ATGAGCCACGGGAAGAGAAC | 7 |
| Ddit3 | NM_007837 | TCGCTCTCCAGATTCCAGTC | 9 |
| Il12a | NM_001159424 | TGATGATGACCCTGTGCCTT | 11 |
| Mapt | NM_001285455 | TAGCAACGTCCAGTCCAAGT | 13 |
| Mnda | NM_001033450 | GACAACCAAGAGCAATACACCA | 15 |
| Nod1 | NM_172729 | GAAGGCACCCCATTGGGTT | 17 |
| Prkcz | NM_008860 | GCGTGGATGCCATGACAAC | 19 |
| Tnfrsf19 | NM_013869 | GCATGCTGTCAGTATCACCG | 21 |

| Gene | Backward (5'→3') | Sequence Identifier |
|---|---|---|
| Adm | GTTGTGTTCTGCTCGTCCAG | 2 |
| Bik | CCTTCATGCTGGGAGTCTCA | 4 |
| Bmf | AATGGGTGAGAGGGAAGAGC | 6 |
| Btg2 | GCCCTACTGAAAACCTTGAGTC | 8 |
| Ddit3 | GCTCTTCCTCCTCTTCCTCC | 10 |
| Il12a | TTGATGGCCTGGAACTCTGT | 12 |
| Mapt | TCCTGGCTTGTGATGGATGT | 14 |
| Mnda | ATCAGTTTGCCCAATCCAGAAT | 16 |
| Nod1 | AATCTCTGCATCTTCGGCTGA | 18 |
| Prkcz | AATGATGAGCACTTCGTCCCT | 20 |
| Tnfrsf19 | CAGCACAAGGACGGAATCAG | 22 |

The ASCII text file of the sequence listing named SequenceListingapp.txt which is 5 KB in size and was created on Jun. 29, 2016 is incorporated by reference herein in its entirety.

The results of measurement of RNA-level expression of apoptosis regulatory genes upon irradiation are shown in FIGS. 1A to 1D.

Upon low-dose-rate low-level irradiation, among the apoptosis regulatory genes selected in Example 2-1, genes, the RNA-level expression of which was increased compared to the non-irradiated cell group, were detected. The detected genes were Adm, Btg2, Il12a, Mnda, Bmf, Nod1, Bik, Ddit3, and Tnfrsf19.

In the high-dose-rate low-level-irradiated cell group and the high-dose-rate high-level-irradiated cell group, the apoptosis regulatory gene tended to decrease in RNA-level expression.

Example 3

Measurement of Expression of Apoptosis Regulatory Protein of Irradiated Mouse Thymic Lymphoma Cells In order to measure protein expression of the apoptosis regulatory gene detected in Example 2-2, Western blotting was performed.

A cell lysis buffer was prepared by mixing 150 mM NaCl, 1% Triton X0199, 0.1% SDS, 0.5% sodium deoxycholate, 50 mM Tris (pH 7.4) and 1 mM EDTA. Also, the prepared cell lysis buffer was added with a protease inhibitor (Thermo Scientific, USA) at a concentration of 1% based on the total concentration of the solution.

The low-dose-rate low-level-irradiated cell group of Example 1 was mixed with the cell lysis buffer, and thus the cells were lysed to give a protein sample. Western blotting was performed using the protein sample, and the amount of protein expression was measured. Upon Western blotting, an antibody (1:200, Abcam, Cambridge, Mass.) for detecting Ddit3 and Tnfrsf19 and an antibody (1:200, OriGene) for detecting Nod1, Bmf, and Bik were used.

Also, in the high-dose-rate low-level-irradiated cell group and the high-dose-rate high-level-irradiated cell group of Example 1, the amount of apoptosis regulatory protein expression was measured in the same manner as above.

Figure 2:
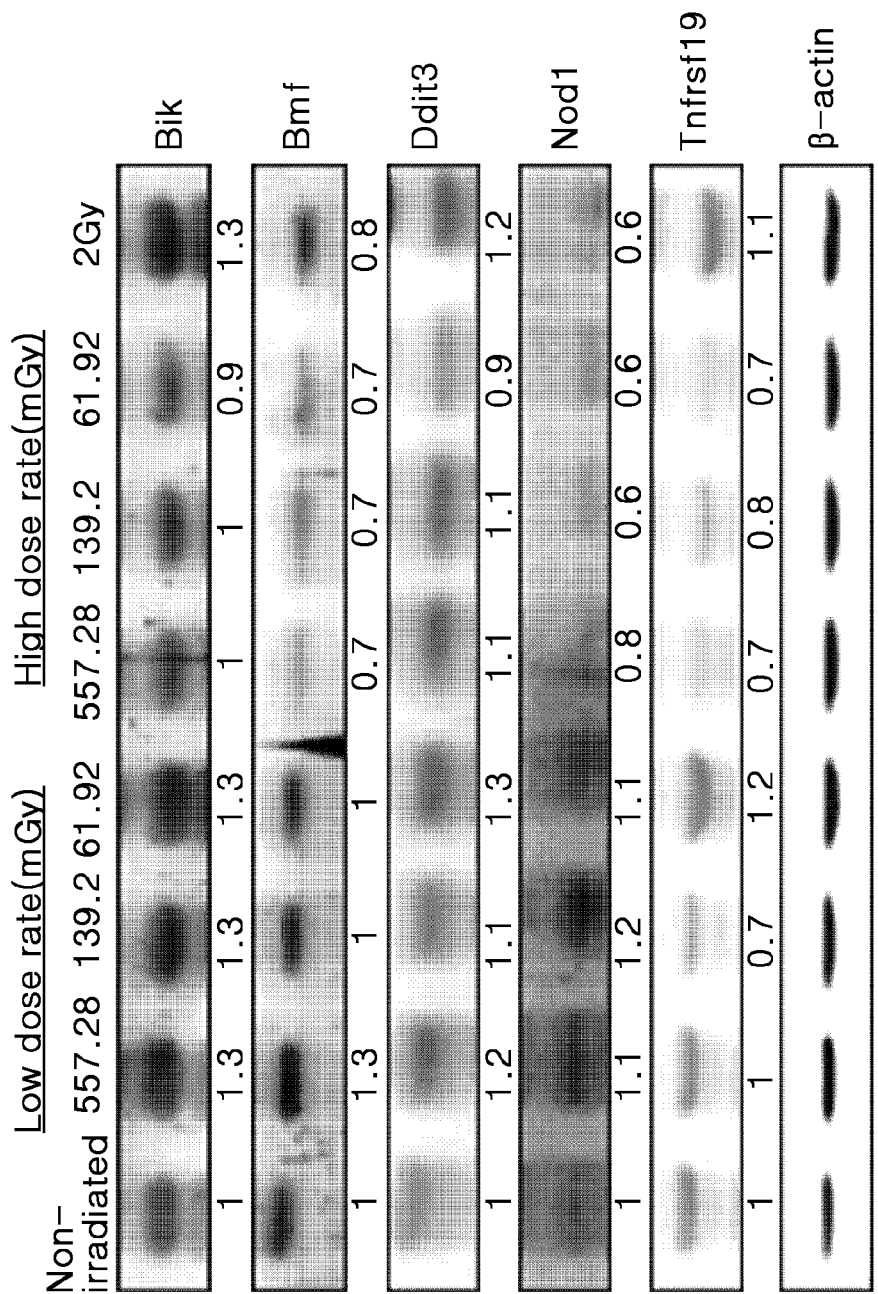
FIG. 2 shows changes in apoptosis regulatory protein expression depending on the dose rate and the cumulative dose.

The results of measurement of the amount of apoptosis regulatory protein expression upon irradiation are shown in FIG. 2. In the low-dose-rate low-level-irradiated cell group, Bmf, Nod1, Bik, Ddit3 and Tnfrsf19, which are the apoptosis regulatory proteins, were increased in protein expression compared to the non-irradiated group.

Figure 3:
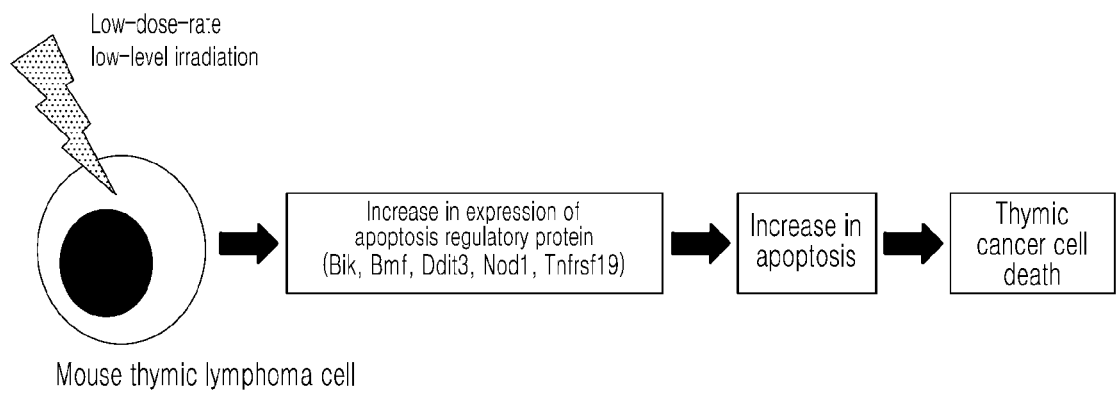
FIG. 3 shows molecular changes due to low-dose-rate low-level irradiation in mouse thymic lymphoma cells and the resulting cancer suppression mechanism.

Based on the above results, apoptosis regulatory genes, the RNA-level expression and protein-level expression of which were increased when applying the low-dose-rate low-level radiation to mouse thymic lymphoma cells, were detected. The detected genes were Bmf, Nod1, Bik, Ddit3, and Tnfrsf19. The detected apoptosis regulatory genes were increased in RNA-level expression and protein-level expression when applying the low-dose-rate low-level radiation to mouse thymic lymphoma cells, thus promoting apoptosis to thereby suppress thymic lymphoma (FIG. 3).

Although the preferred embodiments of the present invention have been disclosed for illustrative purposes, those skilled in the art will appreciate that these embodiments are merely set forth to illustrate but are not to be construed to limit the scope of the present invention. Therefore, the substantial scope of the present invention will be defined by the appended claims and their equivalents.

What is claimed is:

1. A method of detecting an apoptosis regulatory gene in mouse thymic lymphoma cells, comprising:
   applying low-dose-rate low-level radiation to mouse thymic lymphoma cells; and
   detecting an up-regulated expression of an apoptosis regulatory gene in individual irradiated mouse thymic lymphoma cells, wherein the apoptosis regulatory gene is Bik and the low-dose-rate low-level radiation is applied such that a final cumulative dose is 139.2 mGy at a dose rate of 5.8 mGy/hr.

2. The method of claim 1, wherein the mouse thymic lymphoma cells are a mouse thymic lymphoma EL4 cell line.

3. The method of claim 1, wherein the detecting the apoptosis regulatory gene includes performing polymerase chain reaction and Western blotting.

* * * * *

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Adm(NM_009627) Forward Primer

<400> SEQUENCE: 1
tcgctgatga gacgacagtt                                              20

<210> SEQ ID NO 2
<211> LENGTH: 20
<212> TYPE: DNA
<213> ORGANISM: Artificial Sequence
<220> FEATURE:
<223> OTHER INFORMATION: Adm(NM_009627) Backward Primer

<400> SEQUENCE: 2
gttgtgttct gctcgtccag                                              20

<210> SEQ ID NO 3
<211> LENGTH: 20
<212> TYPE: DNA
<213> ORGANISM: Artificial Sequence
<220> FEATURE:
<223> OTHER INFORMATION: Bik(NM_007546) Forward Primer

<400> SEQUENCE: 3
atggccagag acgtcatcaa                                              20

<210> SEQ ID NO 4
<211> LENGTH: 20
<212> TYPE: DNA
<213> ORGANISM: Artificial Sequence
<220> FEATURE:
<223> OTHER INFORMATION: Bik(NM_007546) Backward Primer

<400> SEQUENCE: 4
ccttcatgct gggagtctca                                              20

<210> SEQ ID NO 5
<211> LENGTH: 20
<212> TYPE: DNA
<213> ORGANISM: Artificial Sequence
<220> FEATURE:
<223> OTHER INFORMATION: Bmf(NM_138313) Forward Primer

<400> SEQUENCE: 5
ctctctgctg acctgtttgc                                              20

<210> SEQ ID NO 6
<211> LENGTH: 20
<212> TYPE: DNA
<213> ORGANISM: Artificial Sequence
<220> FEATURE:
<223> OTHER INFORMATION: Bmf(NM_138313) Backward Primer
```

<400> SEQUENCE: 6
aatgggtgag agggaagagc                                          20

<210> SEQ ID NO 7
<211> LENGTH: 20
<212> TYPE: DNA
<213> ORGANISM: Artificial Sequence
<220> FEATURE:
<223> OTHER INFORMATION: Btg2(NM_007570) Forward Primer

<400> SEQUENCE: 7
atgagccacg ggaagagaac                                          20

<210> SEQ ID NO 8
<211> LENGTH: 22
<212> TYPE: DNA
<213> ORGANISM: Artificial Sequence
<220> FEATURE:
<223> OTHER INFORMATION: Btg2(NM_007570) Backward Primer

<400> SEQUENCE: 8
gccctactga aaaccttgag tc                                       22

<210> SEQ ID NO 9
<211> LENGTH: 20
<212> TYPE: DNA
<213> ORGANISM: Artificial Sequence
<220> FEATURE:
<223> OTHER INFORMATION: Ddit3(NM_007837) Forward Primer

<400> SEQUENCE: 9
tcgctctcca gattccagtc                                          20

<210> SEQ ID NO 10
<211> LENGTH: 20
<212> TYPE: DNA
<213> ORGANISM: Artificial Sequence
<220> FEATURE:
<223> OTHER INFORMATION: Ddit3(NM_007837) Backward Primer

<400> SEQUENCE: 10
gctcttcctc ctcttcctcc                                          20

<210> SEQ ID NO 11
<211> LENGTH: 20
<212> TYPE: DNA
<213> ORGANISM: Artificial Sequence
<220> FEATURE:
<223> OTHER INFORMATION: Il12a(NM_001159424) Forward Primer

<400> SEQUENCE: 11
tgatgatgac cctgtgcctt                                          20

<210> SEQ ID NO 12
<211> LENGTH: 20
<212> TYPE: DNA
<213> ORGANISM: Artificial Sequence
<220> FEATURE:
<223> OTHER INFORMATION: Il12a(NM_001159424) Backward Primer

<400> SEQUENCE: 12
ttgatggcct ggaactctgt                                          20

<210> SEQ ID NO 13

-continued

```
<211> LENGTH: 20
<212> TYPE: DNA
<213> ORGANISM: Artificial Sequence
<220> FEATURE:
<223> OTHER INFORMATION: Mapt(NM_001285455) Forward Primer

<400> SEQUENCE: 13
tagcaacgtc cagtccaagt                                           20

<210> SEQ ID NO 14
<211> LENGTH: 20
<212> TYPE: DNA
<213> ORGANISM: Artificial Sequence
<220> FEATURE:
<223> OTHER INFORMATION: Mapt(NM_001285455) Backward Primer

<400> SEQUENCE: 14
tcctggcttg tgatggatgt                                           20

<210> SEQ ID NO 15
<211> LENGTH: 20
<212> TYPE: DNA
<213> ORGANISM: Artificial Sequence
<220> FEATURE:
<223> OTHER INFORMATION: Mnda(NM_001033450) Forward Primer

<400> SEQUENCE: 15
ttgatggcct ggaactctgt                                           20

<210> SEQ ID NO 16
<211> LENGTH: 22
<212> TYPE: DNA
<213> ORGANISM: Artificial Sequence
<220> FEATURE:
<223> OTHER INFORMATION: Mnda(NM_001033450) Backward Primer

<400> SEQUENCE: 16
atcagtttgc ccaatccaga at                                        22

<210> SEQ ID NO 17
<211> LENGTH: 19
<212> TYPE: DNA
<213> ORGANISM: Artificial Sequence
<220> FEATURE:
<223> OTHER INFORMATION: Nod1(NM_172729) Forward Primer

<400> SEQUENCE: 17
gaaggcaccc cattgggtt                                            19

<210> SEQ ID NO 18
<211> LENGTH: 21
<212> TYPE: DNA
<213> ORGANISM: Artificial Sequence
<220> FEATURE:
<223> OTHER INFORMATION: Nod1(NM_172729) Backward Primer

<400> SEQUENCE: 18
aatctctgca tcttcggctg a                                         21

<210> SEQ ID NO 19
<211> LENGTH: 19
<212> TYPE: DNA
<213> ORGANISM: Artificial Sequence
<220> FEATURE:
<223> OTHER INFORMATION: Prkcz(NM_008860) Forward Primer

<400> SEQUENCE: 19
```

```
gcgtggatgc catgacaac                                                    19

<210> SEQ ID NO 20
<211> LENGTH: 21
<212> TYPE: DNA
<213> ORGANISM: Artificial Sequence
<220> FEATURE:
<223> OTHER INFORMATION: Prkcz(NM_008860) Backward Primer

<400> SEQUENCE: 20
aatgatgagc acttcgtccc t                                                 21

<210> SEQ ID NO 21
<211> LENGTH: 20
<212> TYPE: DNA
<213> ORGANISM: Artificial Sequence
<220> FEATURE:
<223> OTHER INFORMATION: Tnfrsf19(NM_013869) Forward Primer

<400> SEQUENCE: 21
gcatgctgtc agtatcaccg                                                   20

<210> SEQ ID NO 22
<211> LENGTH: 20
<212> TYPE: DNA
<213> ORGANISM: Artificial Sequence
<220> FEATURE:
<223> OTHER INFORMATION: Tnfrsf19(NM_013869) Backward Primer

<400> SEQUENCE: 22
cagcacaagg acggaatcag                                                   20
```